United States Patent [19]
McDowell

[11] Patent Number: 5,108,441
[45] Date of Patent: Apr. 28, 1992

[54] METHOD OF REGENERATING JOINT ARTICULAR CARTILAGE

[76] Inventor: Charles L. McDowell, 6425 Roselawn Rd., Richmond, Va. 23226

[21] Appl. No.: 554,289

[22] Filed: Jul. 17, 1990

[51] Int. Cl.⁵ .................. A61F 2/40; A61F 2/30; A61F 2/38
[52] U.S. Cl. ........................... 623/19; 623/18; 623/20
[58] Field of Search ............... 623/16, 18-20, 623/22, 23

[56] References Cited

U.S. PATENT DOCUMENTS

| | | | |
|---|---|---|---|
| 4,198,712 | 4/1980 | Swanson | 623/21 |
| 4,242,758 | 1/1981 | Amis et al. | 623/20 |
| 4,285,071 | 8/1981 | Nelson et al. | 623/22 |
| 4,385,404 | 5/1983 | Sully et al. | 623/18 |
| 4,417,571 | 11/1983 | Nelson et al. | 623/22 X |
| 4,566,138 | 1/1986 | Lewis et al. | 623/22 |

FOREIGN PATENT DOCUMENTS 2933174  4/1980  Fed. Rep. of Germany ........ 623/18

OTHER PUBLICATIONS

"Articular Cartilage Regeneration in the Canine," S. M. Fiore et al.; 8th Southern Biomedical Engineering Conference Digest of Papers-Richmond, VA; Oct. 1989, pp. 178-181.

Primary Examiner—Ronald Frinks
Attorney, Agent, or Firm—Barnes & Thornburg

[57] ABSTRACT

A method and apparatus of facilitating the regeneration of articular cartilage in a joint is disclosed. Regeneration of damaged articular cartilage is facilitated by placing one or more spacers between the articulating surfaces of the joint. The spacers are left in place while the articular cartilage regenerates. The spacers prevent the articulating surfaces from rubbing against each other and the articular cartilage can regenerate in the space between the articulating surfaces. A spacer formed in accordance with this invention has a head with a shaft extending therefrom. The shaft is inserted into one of the articulating surfaces so that the head is disposed between the articulating surfaces and keeps them separated while the articular surface regenerates.

9 Claims, 2 Drawing Sheets

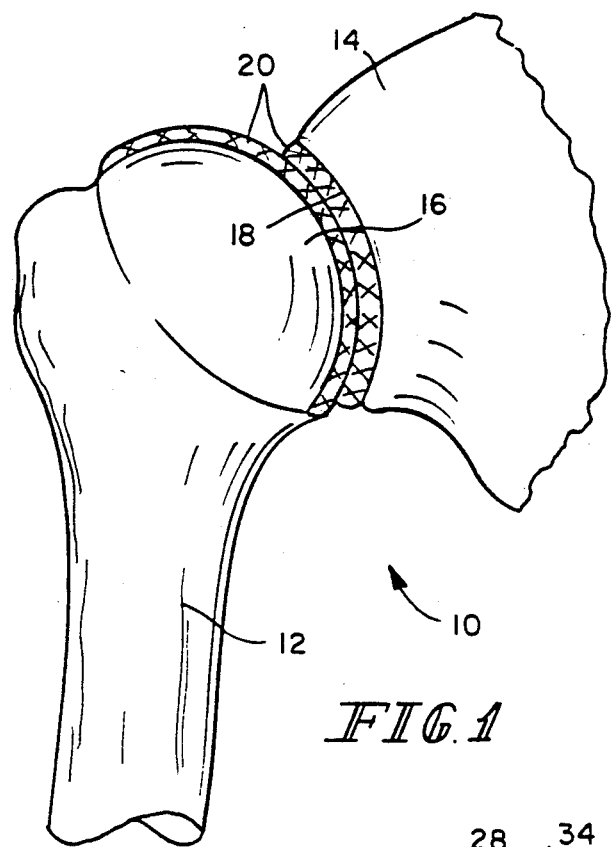
FIG. 1
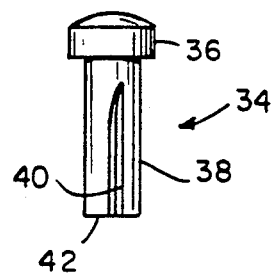
FIG. 3
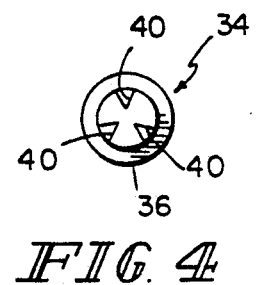
FIG. 4
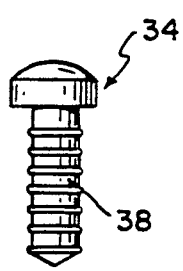
FIG. 7
FIG. 6
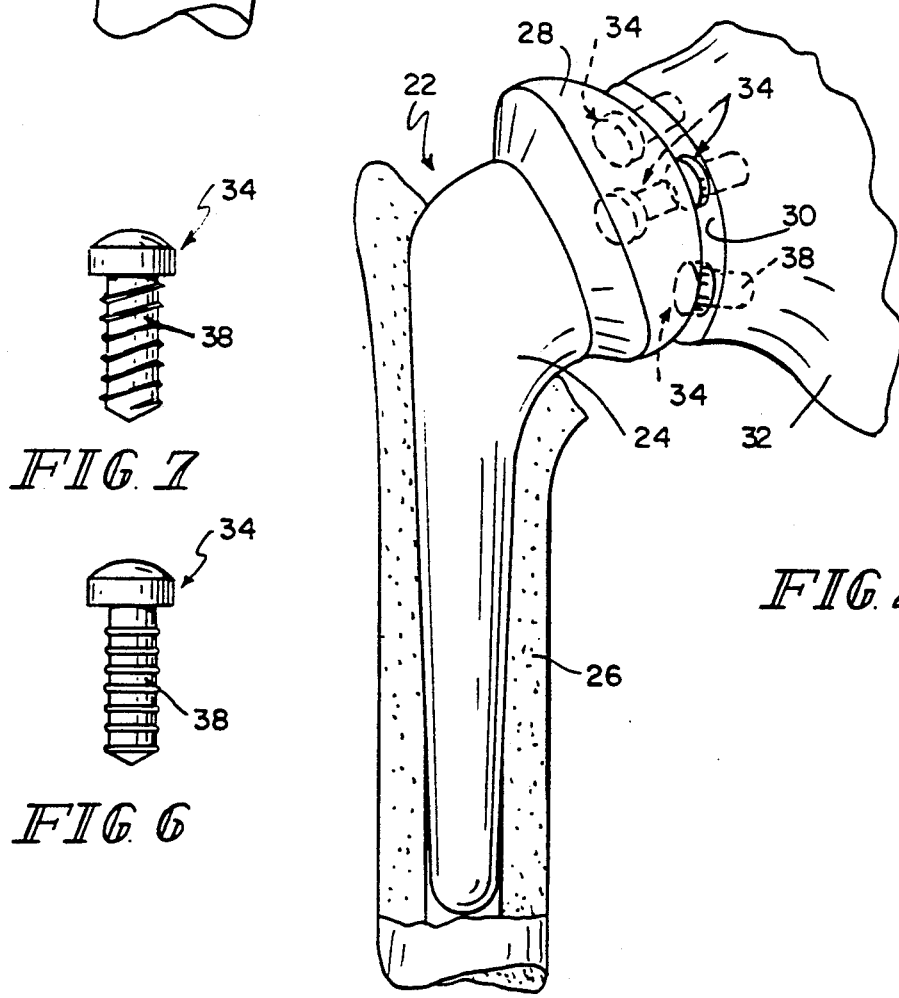
FIG. 2

METHOD OF REGENERATING JOINT ARTICULAR CARTILAGE

BACKGROUND AND SUMMARY OF THE INVENTION

This invention relates to the repair of joints in a body, and more particularly to facilitating the regeneration of articular cartilage in a joint.

The human body has a variety of different joints. These joints comprise two or more bones that have surfaces which articulate with respect to each other. These surfaces are typically called articulating surfaces. However, the articulating surfaces do not physically ride on each other. In a healthy joint, the articulating surfaces are separated by cartilage, commonly called articular cartilage.

A problem arises when the articular cartilage in a joint is damaged because it typically does not regenerate. Articular cartilage can be damaged by diseases such as osteoarthritis, chondromalacia and rheumatoid arthritis. It can also be damaged by fractures which pass through an articular cartilage surface or due to a blow to the joint which causes the articular cartilage to split or causes contusion of the articular cartilage.

When the articular cartilage is damaged, the joint is subjected to increased friction. This causes relatively rapid degeneration of the remaining articular cartilage. This is followed by degenerative changes in the articulating surfaces of the bones in the joint when they become exposed which results in symptoms of pain.

One method of treating the above-described conditions has been to replace the damaged joint with an artificial one. However, this requires a relatively major operation and the resulting trauma to the patient often requires a fairly lengthy recovery. In cases where the bones of the joints remain in relatively good condition, it would be desirable to create a condition within the joint which would facilitate regeneration of the articular cartilage.

As has been mentioned, damaged articular cartilage usually does not regenerate. Studies done by Shands in the early 1930's, and later by Bennett, showed that simple wounding of articular cartilage resulted in a minimal and inadequate healing response. However, if the wound extended through the articular cartilage and into the subchondral bone, there was a healing response. [G. A. Bennett, W. Bauer, "Further Studies Concerning the Repair of Articular Cartilage in Dog Joints," *Journal of Bone and Joint Surgery*, 17:141-150 (1935); A. R. Shands, "The Regeneration of Hyaline Cartilage in Joints, an Experimental Study," *Archives of Surgery*, 22:137-179 (1931).

Replacement of shoulder joints with prosthesis devices present a unique problem due to the nature of the shoulder joint. The shoulder joint is a successful anatomic compromise toward motion and away from stability. This is just the opposite compromise from the hip joint. Because of this, the bone structure of the shoulder joint is that of a ball with a very shallow socket (glenoid). Also, because humans do not bear weight on their shoulder, there is no need for the shoulder joint to have a heavy, strongly constructed deep socket such as found in the hip joint. The problem this creates with respect to replacing the shoulder joint with prosthesis devices is that the structure supporting the shallow glenoid socket is too delicate to consistently support the prostheses which have been used to replace the glenoid.

It is therefore an objective of this invention to facilitate regeneration of damaged articular cartilage by providing a favorable environment in which regeneration can take place.

It is an objective of this invention to facilitate regeneration of damaged articular cartilage by keeping separated the articulating surfaces of the joint during the time when the articular cartilage is regenerating.

It is also an object of this invention to provide a glenoid "prosthesis" for a shoulder joint by implanting a plurality of domed spacers in the natural glenoid to bear the load applied by the humeral head of a humerus.

According to the method and apparatus of this invention, regeneration of damaged articular cartilage is facilitated by placing one or more spacers between the articulating surfaces of the joint. The spacers are left in place while the articular cartilage regenerates. The spacers prevent the articulating surfaces from rubbing against each other and the articular cartilage can regenerate in the space between the articulating surfaces. A spacer formed in accordance with this invention has a head with a shaft extending therefrom. The shaft is inserted into one of the articulating surfaces so that the head is disposed between the articulating surfaces and keeps them separated while the articular surface regenerates.

Spacers formed in accordance with this invention can be used as a glenoid "prosthesis" in a shoulder joint. A plurality of such spacers, illustratively four, are implanted in the natural glenoid of a shoulder joint. These spacers bear the load of the humeral head of a humerus. These spacers preferably have domed heads.

Other objects, advantages and novel features of the present invention will become apparent from the following detailed description of the invention when considered in conjunction with the accompanying drawings.

BRIEF DESCRIPTION OF THE DRAWINGS

FIG. 1 is a perspective view of a shoulder joint;

FIG. 2 is a perspective view of a shoulder joint using the spacers of this invention as a glenoid prosthesis; and FIG. 3 is a side perspective view of a spacer formed in accordance with this invention;

FIG. 4 is a bottom view of the spacer of FIG. 3;

FIG. 6 is a side perspective view of a spacer formed in accordance with the invention having flexible flanges; and FIG. 7 is a side perspective view of a spacer formed in accordance with the invention that is threaded.

DETAILED DESCRIPTION OF THE DRAWINGS

Figure 5:
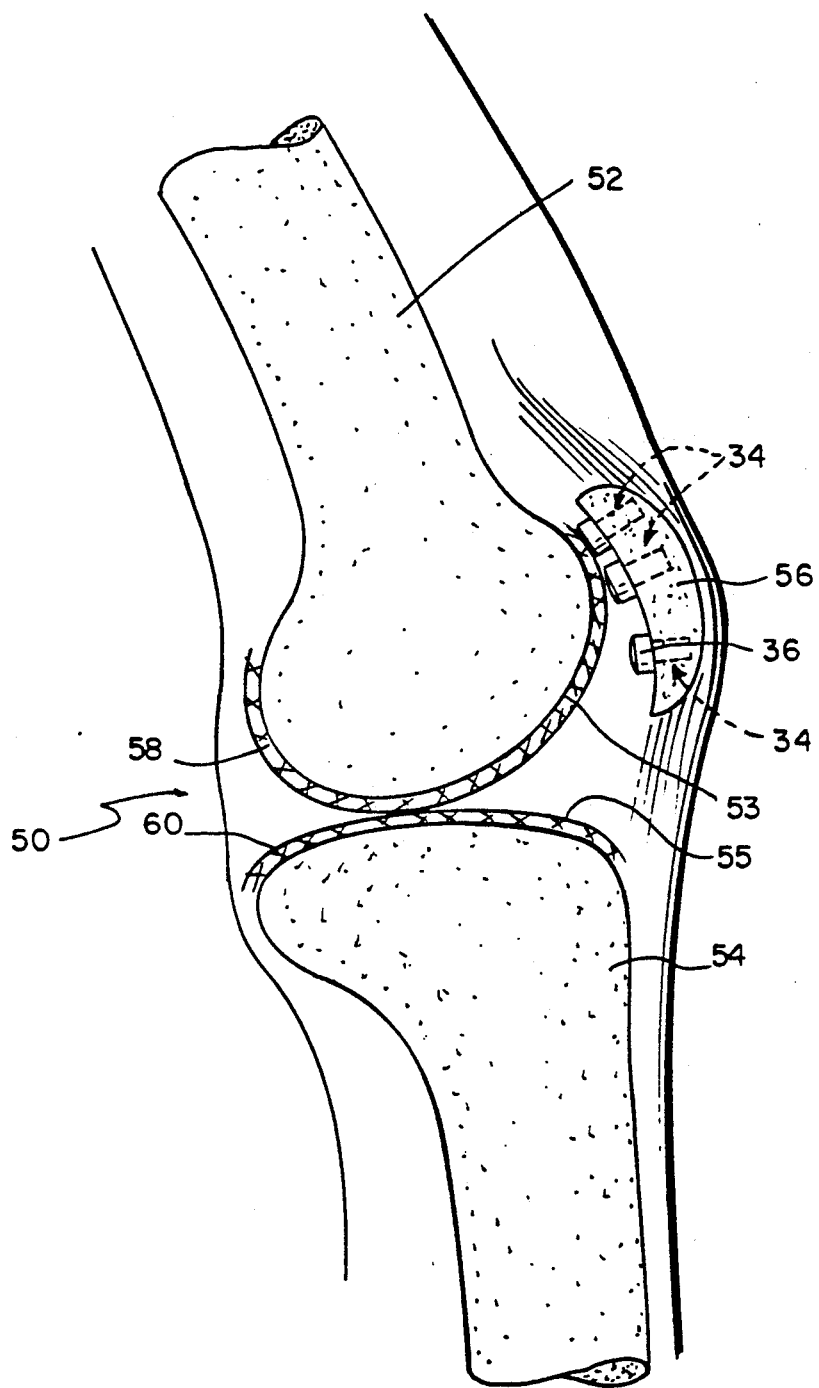
FIG. 5 is a perspective view of a knee joint using the spacers of this invention.

Referring to FIG. 1, a shoulder joint 10 is shown to illustrate the salient features of joints in the human body as they relate to this invention. Shoulder joint 10 has a humerus 12 and a scapula 14 having a glenoid 18. Humerus 12 has at one end a ball 16 which is received in glenoid 18. The surfaces of ball 16 and glenoid 18 comprise the articulating surfaces of shoulder joint 10. As is the case in normal, healthy joints, the surfaces of ball 16 and glenoid 18 each have thereon a layer of articular cartilage 20 shown by the cross-hatching. Articular cartilage 20 separates the articulating surfaces of ball 16 and glenoid 18.

As mentioned previously, articular cartilage 20 can be damaged by disease or injury. If the damage is severe enough, there will not be sufficient articular cartilage 20 left between the articulating surfaces of shoulder joint 10 to keep the articulating surfaces separated. The resulting increase in friction and mechanical stress in shoulder joint 10 will cause the remaining articular cartilage 20 to deteriorate rather rapidly. This increased friction and mechanical stress also precludes the articular cartilage 20 from regenerating. Consequently, the articulating surface of shoulder joint 10, i.e., the surfaces of ball 16 and glenoid 18, will then come into physical contact with each other. This results in pain and also causes the surfaces of ball 16 and glenoid 18 to deteriorate.

As discussed, the entire joint is often replaced to alleviate the above-described condition. The artificial joint used frequently has a metal articulating surface and a high density polyethylene articulating surface. However, the operation to replace the joint is fairly traumatic to the patient. Also, articular cartilage, which would enhance the functioning of such an artificial joint, cannot form between the articulating surfaces for the same reasons as discussed above. Additionally, in some cases only one of the articulating surfaces of the joint has degenerated to the point where it must be replaced. In such cases, it is desirable to use the natural undamaged articulating surface and replace only the damaged one. However, lack of undamaged articular cartilage might prevent this if the articulation of the natural bone articulating surface against the artificial articulating surface would cause the bone to degenerate.

Referring to FIGS. 2-4, the method and apparatus of this invention which creates a condition favorable to the regeneration of articular cartilage is described. Referring particularly to FIG. 2, a shoulder joint 22 in which this invention is used is shown. Shoulder joint 22 has an artificial humeral component 24 implanted in humerus 26. Humeral component 24 has a ball 28 at a proximal end which is received in a glenoid 30 of scapula 32. Scapula 32 is, in this example, the natural scapular bone. The surfaces of ball 28 and glenoid 30 comprise the articulating surfaces of shoulder joint 22.

A plurality of spacers 34 are disposed between the articulating surfaces of shoulder joint 22. Spacers 34 keep the articulating surfaces separated. This facilitates the regeneration of articular cartilage between the articulating surfaces in shoulder joint 22. Articular cartilage can form in the space between the articulating surfaces. Spacers 34 prevent the regenerating articular cartilage from being destroyed by being sandwiched between the articulating surfaces of shoulder joint 22.

Referring to FIGS. 3 and 4, spacer 34 is described in greater detail. Spacer 34 is illustratively formed from ultra-high, molecular weight polypropylene or other appropriate material. Spacer 34 has a head 36 from which a shaft 38 extends. Head 36 is illustratively convex or domed although it could also be other shapes such as flat or concave. Shaft 38 has a plurality of slots 40 formed therein. Slots 40 extend axially in shaft 38 from a distal end 42 of shaft 38 part way toward head 36. Slots 40 facilitate insertion of shaft 38 of spacer 34 into an articulating surface of the joint. As shown in FIG. 2, shaft 38 of spacer 34 is inserted into the bone of scapula 32 such that the head 36 is disposed between the articulating surface which is the surface of ball 28 and the articulating surface which is the surface of glenoid 30. Spacers 34 can be cemented in place. Alternatively, shafts 38 of spacers 34 can have flexible flanges (FIG. 6) to permit spacers 34 to be press-fit in place, or could be slotted or serrated. Also, shafts 38 could be threaded to permit spacers 34 to be screwed into place (FIG. 7).

Referring to FIG. 2, the spacers 34 are used as a glenoid "prosthesis." That is, spacers 34 take the place of a glenoid prosthesis and bear the load of ball 28 of humeral component 24. Spacers 34 could also be used as a glenoid "prosthesis" where the natural humerus is left in place. Preferably, the heads 36 of spacers 34 used as shown in FIG. 2 are domed.

The relatively smaller size of spacers 34 when compared to a glenoid prosthesis, as well as the shape of the spacers, will likely reduce the complications of dislocations which occur when a glenoid prosthesis is implanted. Further, the operation to insert a total shoulder prosthesis is a difficult and exacting one. Use of spacers 34 in lieu of a glenoid prosthesis will likely make the operation easier and thus safer for the patient.

In accordance with this invention, spacers 34 can be used as temporary separators of joint surfaces, such as in the shoulder joint, knee joint, elbow joint, finger joints, thumb joints, wrist joint, etc., to allow new cartilage growth. Referring to FIG. 5, spacers 34 are shown in the patello-femoral portion of a knee joint 50 to permit cartilage to grow between a femur 52 and a patella 56 of knee joint 50. Knee joint 50 has a femur 52, a tibia 54, and a patella 56. In the example of FIG. 5, the cartilage between patella 56 and femur 52 has become damaged and can no longer separate the patello-femoral joint surfaces. However, cartilage 58 on condyles 53 of femur 52 and cartilage 60 on a top surface 55 of tibia 54 are still healthy. When spacers 34 are implanted in patella 56, the cartilage between patella 56 and condyles 53 of femur 52 is removed and the spacers 34 then implanted in patella 56. Cartilage 58 and 60 which separates the condyles 53 of femur 52 from the top surface 55 of tibia 54 is left in place.

Spacers 34 are implanted in patella 56 such that the heads 36 of spacers 34 are disposed between the condyles 53 of femur 52 and an inner surface of patella 56. Spacers 34 permit cartilage to grow between patella 56 and the condyles 53 of femur 52. After new cartilage has grown between patella 56 and condyles 53 of femur 52, the spacers 34 are then removed. This leaves a completely natural knee joint 50 in which the damaged cartilage between patella 56 and the condyles 53 of femur 52 has been replaced by new, healthy cartilage.

Although the invention has been described in detail with reference to certain preferred embodiments and specific examples, variations and modifications exist within the scope and spirit of the invention as described and as defined in the following claims.

What is claimed is:

1. A method of facilitating regeneration of articular cartilage on an articulating surface in a joint, comprising the steps of:

removing damaged articular cartilage from at least a portion of the articulating surface;

positioning a plurality of spacers on the surface in spaced apart relation so as to effectively separate the surface from an adjacent surface; and allowing articular cartilage to regenerate on that portion of the articulating surface from which the damaged cartilage has been removed.

2. A method according to claim 1, including the additional step of removing the spacers after the articular cartilage has regenerated on the articulating surface.

3. A method according to claim 1, wherein each of said spacers comprise a head and means for fixing the head in position on the articulating surface in spaced apart relation so as to allow for natural regeneration of cartilage in the areas between the spaced apart heads of the spacers.

4. A method according to claim 3, wherein said means for fixing the head in position comprises a shaft extending from the head and adapted for insertion into bony tissue underlying one of the articulating surface of the joint.

5. A method according to claim 4, wherein said shaft has an axially extending slot formed therein to facilitate insertion of the shaft into the bony tissue.

6. A method according to claim 4, wherein said shaft has a plurality of flexible flanges formed thereon.

7. A method according to claim 4, wherein said shaft is threaded.

8. A method of facilitating regeneration of articular cartilage in a joint having articulating surfaces, comprising the steps of removing damaged articular cartilage from at least a portion of one of the articulating surfaces of the joint, implanting a plurality of spacers in spaced apart relation between the articulating surfaces so as to effectively separate at least that portion of the surface from which the damaged cartilage is removed from the adjacent surface, and leaving the spacers in place for a time sufficient to allow for regeneration of cartilage on said portion of the articulating surface.

9. A method according to claim 8, including the additional step of removing the spacers after regeneration of the articular cartilage.

* * * * *